United States Patent
Van Arsdell et al.

(10) Patent No.: US 6,737,256 B2
(45) Date of Patent: May 18, 2004

(54) OVERCOMING DAPA AMINOTRANSFERASE BOTTLENECKS IN BIOTIN VITAMERS BIOSYNTHESIS

(75) Inventors: Scott W. Van Arsdell, Lexington, MA (US); R. Rogers Yocum, Lexington, MA (US); John B. Perkins, Reading, MA (US); Janice G. Pero, Lexington, MA (US)

(73) Assignee: Roche Vitamins Inc., Parsippany, NJ (US)

( * ) Notice: Subject to any disclaimer, the term of this patent is extended or adjusted under 35 U.S.C. 154(b) by 53 days.

(21) Appl. No.: 08/914,332

(22) Filed: Jul. 14, 1997

(65) Prior Publication Data

US 2002/0098556 A1 Jul. 25, 2002

(51) Int. Cl.$^7$ .......................... C12P 17/18; C12P 13/00; C12N 1/20; C12N 9/10; C12N 15/00

(52) U.S. Cl. .................. 435/119; 435/252.31; 435/128; 435/130; 435/193; 435/440; 435/320.1; 536/23.2

(58) Field of Search .......................... 435/119, 252.31, 435/128, 130, 193, 440, 320.1; 536/23.2

(56) References Cited

U.S. PATENT DOCUMENTS

| | | | | |
|---|---|---|---|---|
| 4,563,426 A | * | 1/1986 | Yamada et al. | 435/119 |
| 5,096,823 A | | 3/1992 | Gloeckler et al. | 435/252.31 |
| 5,374,554 A | * | 12/1994 | Komatsubara et al. | 435/252.3 |
| 6,057,136 A | * | 5/2000 | Bower et al. | 435/119 |

FOREIGN PATENT DOCUMENTS

| | | |
|---|---|---|
| EP | 0 635 572 A2 | 6/1994 |
| WO | WO 94/08023 | 4/1994 |

OTHER PUBLICATIONS

Bork, Genome Research, 10:348–400, 2000.*
Broun et al., Science 282:1315–1317, 1998.*
Van de Loo et al., Proc. Natl. Acad. Sci. 92:6743–6747, 1995.*
Phalip et al., Gene 232:43–51, 1999.*
Levy–Schil, S. et al., Appl. Microbiol. Biotech. vol. 38, pp. 755–762.*
Eisenberg, et al., "Biosynthesis of Biotin and Lipoic Acid," in *Escherichia coli and Salmonella typhimurium*, vol. 1, Neidhardt, et al., pp. 544–550 (1987).
Izumi, et al., "7,8–Diaminopelargonic Acid Aminotransferase, an Enzyme Involved in Biotin Biosynthesis by Microorganisms," *Agr. Biol. Chem.*, 39(1), pp. 175–181 (1975).
Sakurai, et al., "Construction of a Biotin–Overproducing Strain of *Serratia marcescens*," Applied and Enviromental Microbiology, vol. 59, No. 9, pp. 2857–2863 (1993).

Birch et al., "Biotin synthase from *Escherichia coli*, an Investigation of the Low Molecular Weight and Protein Components Required for Activity in vitro", J. Biol. Chem., 270:19158–19165, 1995.
Bower et al., "Cloning, Sequencing, and Characterization of the *Bacillus subtilis* Biotin Biosynthetic Operon", J. Bacteriology, 178:4122–4130, 1996.
Cohen, "The Common pathway to Lysine, Methionine, and Threonine", Addison–Wesley Pub. Co., 1983.
Coque et al., "A Gene Encoding Lysine 6–Aminotranferase, Which Forms the β–Lactam Precursor α–Aminoadipic Acid, . . . ", J. Bacteriology, 173:6258–6264, 1991.
Cronan, Jr., "The *E. coli bio* Operon: Transcriptional Repression by an Essential Protein Modification Enzyme", Cell, vol. 58, Minireview, 1989.
Eisenberg et al., "Biosynthesis of 7,8–Diaminopelargonic Acid, a Biotin Intermediate, from 7–Keto–8–Aminopelargonic Acid and S–Adenosyl–L–Methionine", J. Bacteriology, 108:1135–1140, 1971.
Florentin et al., "On the mechanism of biotin synthase of *Bacillus sphaericus*", Sciences de la vie/Life sciences, 317:485–488, 1994.
Fujisawa et al., "Bioconversion of Dethiobiotin into Biotin by Resting Cells and Protoplasts of *Bacillus sphaericus* bioβ Transformat", Biosci. Biotech., 57:740–744, 1993.
Fujisawa et al., "Bioconversion of dethiobiotin to biotin by a cell–free system of a bioYB transformant of *Bacillus sphaericus*", FEMS Microbiol. Letters, 110:1–4, 1993.
Gloeckler et al., "Cloning and characterization of the *Bacillus sphaericus* genes controlling the bioconversion of pimelate into dethiobiotin ", Gene, vol. 87, No. 1, 1990.
Ifuku et al., "Conversion off Dethiobiotin to Biotin in Cell–free Extracts of *Escherichia coli*", Biosci. Biotech. Biochem, 56:1780–1785, 1992.
Izumi et al., "Characterization of Biotin Biosynthetic Enzymes of *Bacillus sphaericus*: a Dethiobiotin producing Bacterium", Agric. Biol. Chem., 45:1983–1989, 1981.
Lowe et al., "Aminotranserase activities in *Trichomas vaginalis*", Mol. Biochem. Parasitology, 20:65–74, 1986.
Masuda et al., "Further Improvement of D–Biotin Production by a Recombinant Strain of *Serratia marcescens*", Process Biochem., 30:553–562, 1995.
Ohshiro et al., "Enzymatic Conversion of Dethiobiotin to Biotin in Cell–free Extracts of a *Bacillus sphaericus* bioB Transformant", Biosci. Biotech. Biochem., 58:1738–1741, 1994.

(List continued on next page.)

Primary Examiner—Rebecca E. Prouty
Assistant Examiner—Delia Raminez
(74) Attorney, Agent, or Firm—Bryan Cave LLP

(57) ABSTRACT

A method is disclosed for the increased production of biotin and the biotin precursor dethiobiotin using a bacterium that produces a lysine-utilizing DAPA aminotransferase. This method involves the use of a bacterium that is either grown in the presence of lysine or deregulated for lysine biosynthesis.

22 Claims, 4 Drawing Sheets

OTHER PUBLICATIONS

Sakurai et al., "Improvement of a d–biotin–hyperproducing recombinant strain of *Serratia marcescens*", J. Biotech., 36:63–73, 1994.

Sanyal et al., "Biotin Synthase: Purification, Characterization as a [2Fe–2S] Cluster Protein, and in Vitro Activity of the *Escherichia coli bioB* Gene Product", Biochem., 33:3625–3631, 1994.

Schmidt et al., "A novel enzyme, L–lysine: pyruvate aminotransferase, catalyses the first step of lysine catabolism in *Pichia guilliermondii*", FEMS Microbiol. Letters, 49:203–206, 1988.

Soda et al., "L–Lysine–α–Ketoglutarate Aminotranferase. I. Identification of a Product, $\Delta^1$–Piperideine–6–carboxylic Acid", Biochem., 7:4102–4109, 1968.

Soda et al., "L–Lysine–α–Ketoglutarate Aminotransferase. II. Purification, Crystallization, and Properties", Biochem., 7:4110–4112, 1968.

Stoner et al., "Biosynthesis of 7,8–Diaminopelargonic Acid from 7–Keto–8–aminopelargonic Acid and *S*–Adenosyl–L–methionine", J. Biol. Chem., 250:4037–4043, 1975.

Stoner et al., "Purification and Properties of 7,8–Diaminopelargonic Acid Aminotransferase", J. Biol. Chem., 250:4029–4036, 1975.

Tobin et al., "Localization of the Lysine ε–Aminotranferase (*lat*) and δ–(L–α–Aminoadipyl)–L–Cysteinyl–D–Valine synthetase (*pcbAB*) Genes . . . ", J. Bacteriology, 173:6223–6229, 1991.

Paulus, "Biosynthesis of the Aspartate Family of Amino Acids," cited in Sonenshien, et al., *Bacillus subtilis and other Gram–Positive Bacteria: Biochemistry, Physiology, and Molecular Genetics*. American Society for Microbiology: Washington, D.C. (1993). pp. 237–267.

Derwent Abstract No. AN 90–195614 of EP 375 525, Jun. 27, 1990.

Chemical Abstracts, vol. 82, No. 19, May 12, 1975, Abstract No. 120648.

Chemical Abstracts, vol. 96, No. 1, Jan. 4, 1982, Abstract No. 2708.

Chemical Abstracts, vol. 83, No. 5, Aug. 4, 1975, Abstract No. 39418.

* cited by examiner

| LANE | SAMPLE (ACID UNAUTOCLAVED) | AMOUNT |
|---|---|---|
| 1 | KAPA - 0.33 mM/63 mg/L | 1 µl |
| 2 | KAPA - 0.13 mM/25 mg/L | 1 µl |
| 3 | KAPA - 0.07 mM/12 mg/L | 1 µl |
| 4 | KAPA - 0.03 mM/6 mg/L | 1 µl |
| 5 | B167 - 30 hr | 1 µl - 1/10 dil. |
| 6 | B168 - 30 hr | 1 µl - 1/10 dil. |
| 7 | B166 - 30 hr | 1 µl - 1/5 dil. |

*A DAPA SPOT NOT SHOWN*

OVERCOMING DAPA AMINOTRANSFERASE BOTTLENECKS IN BIOTIN VITAMERS BIOSYNTHESIS

BACKGROUND OF THE INVENTION

The present invention is in the general field of the biosynthesis of biotin vitamers.

Biotin biosynthesis in *Escherchia coli* and *Bacillus sphaericus* has been studied at both the biochemical and molecular biological levels (DeMoll, 1996. In F. C. Neidhardt et al., (eds.) *E. coli* and *Salmonella typhimurium*: Cellular and Molecular Biology, Second edition ed., vol 1., pp. 704–709, ASM Press, Washington, D.C.; Perkins et al., In A. L. Sonenshein et al. (eds.), In *Bacillus subtilis* and Other Gram Positive Bacteria: Biochemistry, Physiology, and Molecular Genetics, pp. 319–334, American Society for Microbiology, Washington, D.C.; Eisenberg, 1987. In F. Neidhardt et al. (eds.), *E. coli* and *Salmonella typhimurium*, pp. 544–550. American Society for Microbiology, Washington, D.C.; Cronan, Cell 58:427–429, 1989, Izumi et al., Agric. Biol. Chem. 45:1983–1989, 1981; Gloeckler et al., Gene 87:63–70, 1990), although some steps and components in biotin synthesis remain to be elucidated (Ohshiro et al., Biosci. Biotech. Biochem. 58:1738–1741, 1994; Ifuku et al., Eur. J. Biochem. 224:173–178, 1994; Florentin et al., C. R. Acad. Sci. Paris 317:485–488, 1994; Birch et al., J. Biol. Chem. 270:19158–19165, 1995; Sanyal et al., Biochemistry 33:3625–3631, 1995). Several enzymes involved in the conversion of pimeloyl-CoA to biotin have been isolated and characterized from both of these bacterial species (Ploux et al., Biochem. J. 283:327–321, 1992; Izumi et al., Agric. Biol. Chem. 45:1983–1989, 1981; Eisenberg, supra, Huang et al., Biochemistry 34:10985–10995, 1995). KAPA synthase, the product of bioF, catalyzes the conversion of pimeloyl-CoA and alanine to 8-amino-7-ketopelargonic acid (KAPA). DAPA aminotransferase, the product of bioA, then transfers an amino group from a donor to KAPA yielding 7,8-diaminopelargonic acid (DAPA). Dethiobiotin synthetase (bioD) catalyzes the closure of the ureido-ring to produce dethiobiotin (DTB), and finally the product of bioB, biotin synthase, functions together with a number of other components including flavodoxin (Birch et al., supra; Ifuku et al., supra) S-adenosylmethionine (SAM) (Florentin, C. R. Acad. Sci. Paris 317:485–488, 1994; Ohshiro et al., supra; Sanyal et al., supra; Birch et al., supra) ferrodoxin NADP$^+$ reductase (Birch et al., supra; Sanyal et al., Arch. Biochem. Biophys. 326:48–56, 1996) and possibly cysteine (Florentin, C. R. Acad. Sci. Paris 317:485–488, 1994; Birch et al., supra; Sanyal et al., supra) to convert dethiobiotin to biotin. The compounds KAPA, DAPA, DTB, and biotin are collectively or singly referred to as vitamers or biotin vitamers.

In *E. coli* the genes that encode these enzymes are located in two divergently transcribed operons, controlled by a single operator that interacts with the BirA repressor (Cronan, Cell 58:427–429, 1989). In *B. sphaericus*, the genes are located in two separate operons (Gloeckler et al., supra. The early steps of the pathway, those involved in the synthesis of pimeloyl-CoA, are less well understood (Ifuku et al., Eur. J. Biochem. 224:173–178, 1994; Sanyal et al., J. Am. Chem. Soc. 116:2637–2638, 1994). *B. sphaericus* contains an enzyme, pimeloyl-CoA synthetase (bioW) that converts pimelic acid to pimeloyl CoA (Gloeckler et al., Gene 87:63–70, 1990), (Ploux et al., Biochem. J. 287:685–690, 1992). *E. coli* lacks this enzyme and cannot use pimelic acid as an intermediate in biotin synthesis (Gloeckler et al., supra; Ifuku et al., Eur. J. Biochem. 224:173–178, 1994; Sanyal et al., J. Am. Chem. Soc. 116:2637–2638, 1994). *E. coli* contains two genes, bioC which is located in the bio operon and bioH which is unlinked to the other bio genes, that both appear to be involved in the early steps of biotin biosynthesis leading up to pimeloyl-CoA, but their exact roles are unknown (Eisenberg, supra; Lemoine et al., Mol. Micro. 19:645–647, 1996).

*B. subtilis* contains homologs of the *E. coli* and *B. sphaericus* bioA, bioB, bioD, and bioF genes. These four genes along with a homolog of the *B. sphaericus* bioW gene are arranged in a single operon in the order bioWAFDB, and are followed by two additional genes, bioI and orf2 (Bower et al., J. Bacteriol. 178:4122–4130, 1996). bioI and orf2 are generally dissimilar to other known biotin biosynthetic genes. The bioI gene encodes a protein with similarity to cytochrome P450s and is able to complement mutations in either *E. coli* bioC or bioH (Bower et al., supra. Mutations in bioI cause *B. subtilis* to grow poorly in the absence of biotin. The bradytroph phenotype of bioI mutants can be overcome by pimelic acid, suggesting that the product of bioI functions at a step prior to pimelic acid synthesis (Bower et al., supra.

The *B. subtilis* bio operon is preceded by a putative vegetative promoter sequence and contains, just downstream, a region of dyad symmetry with homology to the bio regulatory region of *B. sphaericus* (Bower et al., supra. Analysis of a bioW-lacZ translational fusion indicates that expression of the biotin operon is regulated by biotin and the *B. subtilis* birA gene. Strains deregulated for biotin synthesis can be engineered by replacing the promoter and regulatory region with a constitutive promoter as described in European Patent Application 0635572 A2, incorporated herein by reference. Production of biotin and biotin vitamers can be further improved by integration and amplification of the deregulated genes in the *B. subtilis* chromosome. Strain BI282, in European Patent Application 0635572 A2, herein incorporated by reference, is an example of such a strain.

SUMMARY OF THE INVENTION

We have found that the conversion of KAPA to DAPA is a serious bottleneck in the biosynthesis of biotin using engineered cells that are fed pimelic acid. As other controls on biotin biosynthesis are removed, the KAPA to DAPA conversion is unable to keep pace with KAPA production, resulting in a build-up of KAPA, without a concomitant increase in the final product. We have also discovered that an important component of the bottleneck is the availability and identity of the amino donor used in the KAPA to DAPA conversion. In general, providing adequate quantities of the amino donor is an important strategy for overcoming the bottleneck. Moreover, a DAPA aminotransferase able to use lysine and related compounds as a source of the amino group to be transfered in the reaction which produces DAPA from KAPA, can significantly improve biosynthetic yields of the downstream biotin vitamers, especially dethiobiotin (DTB).

Although we do not wish to be limited to one specific explanation for our finding to the exclusion of other factors, it appears that providing higher levels of an amino donor which can be used by the available aminotransferase substantially ameliorates the bottleneck discussed above. For example, bacterial production of the biotin vitamers by bacteria whose DAPA aminotransferase uses lysine as an amino donor can be dramatically improved by making sufficient lysine available, either by including it in the fermentation medium or by deregulating the lysine biosynthetic pathway. Such a strategy can also be applied to the use of DAPA aminotransferases of *B. subtilis* and close relatives, including members of the cluster of Bacillus spp. represented by *B. subtilis*. The cluster includes, e.g., *B. subtilis, B. pumilus, B. licheniformis, B. amyloliquefaciens, B. megaterium, B. cereus* and *B. thuringiensis*. The members of the *B. subtilis* cluster are genetically and metabolically divergent from the more distantly related Bacillus spp. of clusters represented by *B. sphaericus* and *B. stearothermophilus* (Priest, In *Bacillus subtilis* and Other Gram-Positive Bacteria, supra pp. 3–16, hereby incorporated by reference; Stackebrant, et al. *J. Gen. Micro.* 133:2523–2529, 1987, hereby incorporated by reference).

Accordingly, one aspect of the invention generally features a method of biosynthesizing (e.g., enzymatically or in fermentations using engineered cells) a biotin vitamer by culturing a bacterium that includes a lysine-utilizing DAPA aminotransferase in an environment enriched in lysine, lysine precursor(s), or analog(s). As used herein, "lysine analog" means a compound that can serve as an amino donor for a DAPA amino transferase, e.g., (S)-2-aiminoethyl-L-cysteine. The desired biotin vitamer is then recovered from the environment. The ability of an amino donor to be used with a given aminotransferase may be evaluated in any appropriate assay, including but not limited to a bioassay based on that described by Eisenberg and Stoner (1971, infra) in which a DAPA sensitive strain of *E. coli* is used to measure DAPA aminotransferase activity. Typically, the bacterium will also be deregulated with respect to one or more biotin synthetic pathway steps, e.g., as described in EP 635572, incorporated above. The DAPA aminotransferase may be produced by the cell's wild-type genetic material, by exogenous nucleic acid introduced into the cell, or both.

As used herein, a "lysine-utilizing DAPA aminotransferase" means a DAPA aminotransferase capable of converting 8-amino-7-ketopelargonic acid (KAPA) to diaminopelargonic acid (DAPA) utilizing lysine or a compound that is converted to lysine or a compound that can substitute for lysine as the amino donor.

As used herein, an "environment enriched for" means a bacterial culture in which the concentration of the indicated molecule is greater than that found under standard culture conditions, and greater than is necessary to avoid limiting cell growth in the absence of biotin vitamer overproduction. For example, lysine, a lysine analog, or a lysine precursor may be exogenously added to the culture and totals at least 10 mmoles per liter of culture.

The biotin vitamer product to be recovered and purified can be biotin, dethiobiotin, or diaminopelargonic acid (DAPA). When dethiobiotin or DAPA is recovered, the method may further include the step of converting the recovered dethiobiotin or DAPA to biotin.

In another aspect of the invention a bacterial strain is also engineered to overcome the KAPA-to-DAPA bottleneck by overproducing a DAPA aminotransferase capable of transferring an amino group from an amino donor to 8-amino-7-ketopelargonic acid (KAPA). In a preferred embodiment of this aspect of the invention, the bacterial strain is further engineered to overproduce the biotin vitamer by deregulation of a biotin biosynthetic step other than the KAPA-DAPA step.

To further circumvent the KAPA-to-DAPA bottleneck, the strain may be further engineered to produce multiple DAPA-aminotransferases, relying on different amino donors (e.g., lysine and SAM). These activities may be assayed and distinguished as described in detail below. Briefly, the level of KAPA-to-DAPA conversion may be measured by vitamer bioassays and bioautography of products from bacteria grown in the presence of lysine, methionine, or lysine and methionine.

As used herein, "SAM-utilizing DAPA amino transferase" means a DAPA aminotransferase capable of converting 8-amino-7-ketopelargonic acid (KAPA) to diaminopelargonic acid (DAPA) utilizing S-adenosylmethionine (SAM) or a compound that is converted to SAM or a compound that can substitute for SAM as the amino donor. As used herein, "SAM analog" means a compound that is structurally similar to SAM that can serve as an amino donor for a DAPA amino transferase.

In other embodiments, methionine and lysine, or their analogs are added to the medium.

One way to provide a lysine-rich environment is to enrich the culture with lysine or a lysine homolog that can donate an amino group to KAPA in the DAPA aminotransferase reaction. Lysine homologs include lysine, (S)-2-aminoethyl-L-cysteine (AEC) and other lysine homologs that can serve as amino donors for a DAPA aminotransferase. Another way to provide a lysine-rich environment is to deregulate the bacterium with respect to lysine production by mutating or engineering it to significantly reduce wild-type control over lysine production. For example, deregulation of a lysine synthetic step includes reducing or removing regulation of transcriptional or other expressional control of a lysine synthetic enzyme, or modification of a lysine synthetic enzyme to reduce or remove control over lysine biosynthesis. Deregulation also includes overproducing compounds which are starting materials in the lysine synthetic pathway, and inhibiting biodegradation of lysine (Amino Acids: Biosynthesis and Genetic Regulations, E. Hermann and R. Somerville (eds.) Addison Wesley, Reading, Mass. 1983, pp. 147–172, 213–244, 417).

Deregulation of a biotin synthetic step includes reducing or removing regulation of transcriptional or other expressional control of a biotin synthetic enzyme, or modification of a biotin synthetic enzyme to reduce or remove control over the enzyme-catalyzed biotin synthetic reaction. It can also include overproducing compounds which are starting materials in the biotin synthetic pathway, and inhibiting biodegradation of a desired biotin vitamer.

Bacteria can be engineered by intentionally and specifically altering the wild-type genome to produce a desired biosynthetic phenotype—e.g., to synthesize more lysine than the corresponding wild-type, unengineered organism, or to remove a bottleneck in the biotin biosynthetic pathway.

Conversion of DTB to biotin may be by any means including but not limited to biochemical conversion of DTB to biotin, feeding DTB to bacteria engineered for the bioconversion of DTB to biotin (Fujisawa et al., Biosci. Biotech. Biochem. 57:740–744, 1993), in vitro synthesis of biotin from DTB (Birch et al., J. Biol. Chem. 270:19158–19165, 1995; Fujisawa et al., FEMS Microbiology Letters 110:1–4, 1993; Ifuku et al., Biosci. Biotech. Biochem. 56:1780–1785, 1992; Birch, WO 94/08023) or chemical synthesis.

DESCRIPTION OF TABLES

Figure 1:
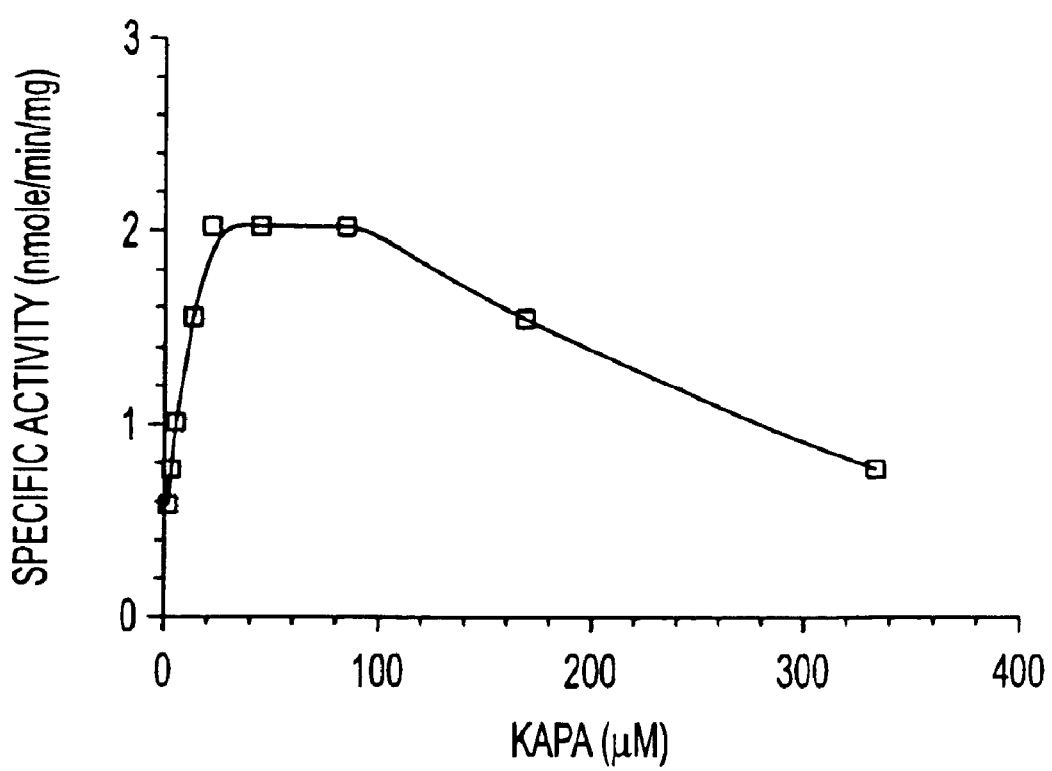
FIG. 1 is a representation of data showing the effect of KAPA concentration on *B. subtilis* DAPA aminotransferase activity.

Table 1 is a representation of the data of a DAPA aminotransferase assay of an extract of BI611 by addition of potential amino donors to the reaction mix.

Table 2 is a representation of the results of a DAPA aminotransferase assay of an extract of BI611 after addition of lysine or lysine-related compounds to the reaction mix.

Table 3 is a representation of biotin and vitamer production of BI282 and BI603 grown in bench scale fermenters in the presence of 6 g lysine/liter.

Table 4 is a representation of biotin and vitamer production of BI282, BI96, and BI90 grown in bench scale fermentors in the presence of 3 g methionine/liter in the batch and feed.

Table 5A–5B represents biotin and vitamer production from strains BI603 and BI90 grown in bench scale fermentors in the presence or absence of 6 g lysine/liter and 3 g methionine/liter.

Table 6 is a representation of results of an assay of biotin and vitamer production using different lysine feed regimens.

Table 7 lists known B. subtilis lysine-deregulated mutants.

Table 8 is a representation of results of an assay of biotin and vitamer production of bacterial strains resistant to AEC grown in the presence of pimelic acid.

Appendix I describes a composition of medium for biotin and vitamer production in bench scale fermentors.

Appendix II describes an avidin-HABA displacement assay for biotin and DTB.

DESCRIPTION OF THE PREFERRED EMBODIMENTS

A bottleneck in KAPA-to-DAPA conversion occurs during pimelic acid-fed fermentations of B. subtilis. In the experiments described below, we discovered that in B. subtilis, DAPA aminotransferase uses lysine as an amino donor, in contrast to S-adenosylmethionine (SAM), the compound that serves as the amino donor for DAPA aminotransferases of B. sphaericus (Izumi et al., Agric. Biol. Chem. 45:1983–1989, 1981), Brevibacterium divaricatum, Salmonella typhimirium, Aerobacter aerogenes, Bacillus roseus, Micrococcus roseus, and Sarcina marginata (Izumi et al., Agr. Biol. Chem. 39:175–181, 1975), E. coli (Eisenberg et al., J. Bacteriol. 108:1135–1140, 1971), and S. marcescens.

In E. coli and B. sphaericus, the conversion of KAPA to DAPA is catalyzed by DAPA aminotransferase, the product of the bioA gene, which utilizes SAM and KAPA as substrates (Eisenberg et al., J. Bacteriol. 108:1135–1140, 1971; Izumi et al., Agric. Biol. Chem. 45:1983–1989, 1981; Stoner et al., J. Biol. Chem. 250:4037–4043, 1975; Stoner et al., J. Biol. Chem. 250:4029–4036). It had been assumed that the reaction was similar in B. subtilis since the B. subtilis aminotransferase is 33% homologous with the E. coli enzyme and can complement bioA mutants in E. coli. However, in vitro assays of the B. subtilis enzyme led to our surprising discovery that lysine is an amino donor for the B. subtilis DAPA aminotransferase. Furthermore, the addition of lysine (2–10 g/l) to the fermentation medium of B. subtilis biotin production strains such as BI282 reduced the amount of KAPA produced and led to the accumulation of significant quantities of dethiobiotin (DTB). Various fermentative or chemical methods can then be used to convert DTB to biotin.

The observation that SAM was not a significant amino donor for the B. subtilis DAPA aminotransferase provided the clue to overcome this bottleneck. A search was made for the real amino donor. After testing 26 different amino acids and related compounds, only lysine was found to dramatically stimulate the in vitro conversion of KAPA to DAPA by the B subtilis DAPA aminotransferase. In subsequent testing, D- and L-lysine and the lysine analog, (S)-2-aminoethyl-L-cysteine (AEC), were found to function as amino donors with the B. subtilis enzyme. Thus, any of these, in any combination, may be used in the invention. Although there are other known aminotransferases that use lysine as an amino donor (Tobin et al., 1991. J. Bacteriol. 173:6223–6229; Coque et al., 1991. J. Bacteriol. 173:6258–6264; Soda et al., 1968. Biochemistry 7:4102–4109; Soda and Misono, 1968, Biochemistry 7:4110–4119; Schmidt et al., 1988, FEMS Microbiol. Lett. 49:203; Lowe and Rowe, 1986. Mol. Biochem. Parasitol. 21:65), no other known DAPA aminotransferase uses lysine. Both the E. coli and the B. sphaericus BioA enzymes use SAM (Eisenberg et al., J. Bacteriol. 108:1135–1140, 1971; Izumi et al., Agric. Biol. Chem. 45:1983–1989, 1981; Stoner et al., J. Biol. Chem. 250:4037–4043, 1975; Stoner et al., J. Biol. Chem. 250:4029–4036).

Characterization of the B. subtilis DAPA aminotransferase indicated that the $K_m$ for lysine was high and, it was substrate inhibited by KAPA. We conclude that the KAPA to DAPA bottleneck was caused by insufficient lysine or an unfavorable ratio of KAPA/lysine, and that the addition of lysine to the fermentation medium could overcome the block.

When fermented with added lysine (6 g/l), as well as pimelic acid (1 g/l), the engineered B. subtilis strain BI282 (bio: $[P_{15}bio]_{7-8}$) showed a dramatic increase (>10-fold) in DTB production. Under these fermentation conditions, BI282 produced about 300–700 mg/l of DTB. Depending on the exact fermentation medium and conditions, nearly all of the KAPA could be converted to DTB. Also, fermentation of strain BI90, a derivative of BI282 that contains a single-copy cassette with the E. coli bioA gene transcribed by the veg promoter of B. subtilis and translated from a synthetic B. subtilis ribosome binding site ($PvegbioA_{ec}$ cassette) in the presence of 6 g/l lysine, 3 g/l methionine (since the E. coli DAPA aminotransferase uses SAM and methionine is the precursor of SAM), and 1 g/l pimelic acid resulted in >90% conversion of KAPA to DTB and high levels of DTB production, 600–900 mg/l. Bioautography was used to confirm the absence of measurable amounts of KAPA. These data indicate that KAPA accumulation is at least partially caused by insufficient intracellular levels of the amino donor in fermentations with added pimelic acid. Increasing the concentration of lysine in the medium overcomes the KAPA to DAPA bottleneck and results in a significant improvement in DTB production.

Figure 4:
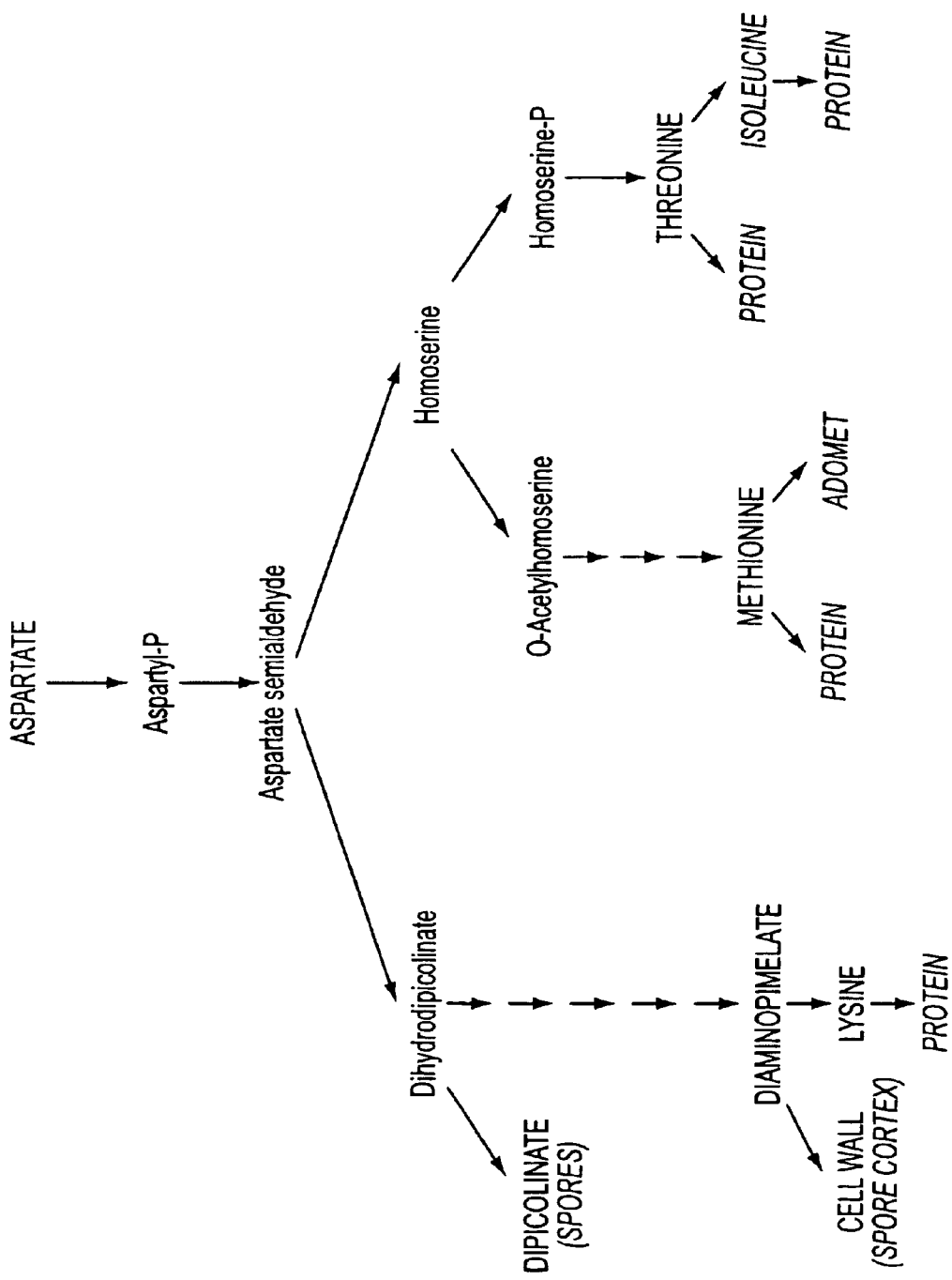
FIG. 4 is a diagram of the B. subtilis biosynthetic pathway for lysine and related compounds.

Mutations can be introduced into BI282 that deregulate the lysine biosynthetic pathway (see FIG. 4). Fermentation experiments of two lysine analog (AEC) resistant mutants of biotin production strains showed improved DTB titers in the absence of added lysine. However, lysine is still limiting in these mutant strains. Additional mutations need to be added to further deregulate lysine biosynthesis if one wishes to eliminate the lysine feed. Such mutations include those that result in 1) deregulated expression of any or all of aspartokinases I, II, or III, 2) feedback resistant aspartokinases I, II, or III, 3) deregulated expression of diaminopimelate decarboxylase, 4) feedback resistant diaminopimelate decarboxylase, or 5) any combination of the above (*Bacillus subtilis* and other Gram Positive Bacteria. (1993) A. Sowenstein J. Hoch, R. Losick (eds.) pp. 237–267. American Society for Microbiology. Washington, D.C.).

DAPA Aminotransferase Enzyme Assay

The assay for DAPA aminotransferase is described by Eisenberg and Stoner in 1971 (*J. Bacteriol.* 108:1135–1140). In this assay, the substrate KAPA is incubated with S-adenosylmethionine (SAM) in the presence of the cofactor pyridoxal 5'-phosphate and cell extract. We measured the amount of DAPA produced in a plate bioassay utilizing an *E. coli* bioA strain. Streptavidin (8 $\mu$g/ml) was added to the assay mix because extracts of many of the strains to be assayed contained significant amounts of biotin and dethiobiotin which fed the *E. coli* indicator strain used in the bioassay. Contamination by trace amounts of biotin and dethiobiotin was also removed from the KAPA preparation used as substrate by passing the material over an avidin-agarose column. The *E. coli* bioA109 strain (MEC1) was used to measure DAPA aminotransferase activity in the bioassay. This *E.coli* bioA strain, developed for the assay by Eisenberg, was reported to be many times more sensitive to DAPA than any other bioA mutant. Eisenberg's DAPA-sensitive strain was obtained from the *E. coli* Genetic Stock Center at Yale University.

*B. subtilis* DAPA Aminotransferase Does Not Utilize SAM as an Amino Donor.

A *B. subtilis* strain, BI282, engineered to overexpress *B. subtilis* BioA protein was assayed for DAPA aminotransferase activity: BI282 contains a $P_{15}$ bio cassette amplified at the bio locus (described in Patent Application 0635572A2). A *B. subtilis* strain deleted for the bio operon, BI9 ($\Delta$bio:neo), was included as negative control. DAPA solutions of known concentration were spotted on the bioassay plates so that the amount of DAPA produced in each assay could be estimated. Measurable DAPA aminotransferase activity was seen in the BI282 extract, but not in the BI9 extract.

The enzyme reaction was approximately linear with time for at least 60 minutes. Using thin layer chromatography, the product of the reaction was shown to be DAPA. Enzyme activity was destroyed by boiling the extract, or freezing and thawing, although freezing the extract in the presence of 10% DMSO appeared to stabilize the enzyme. Activity was dependent on the presence of KAPA, but surprisingly, was not dependent on the presence of SAM. However, extracts assayed from *B. subtilis* strains lacking the native bioA gene but containing a bioA gene derived from either *E. coli* or *S. marcescens*, had DAPA aminotransferase activity dependent on the presence of exogenous SAM. We conclude that the *B. subtilis* DAPA aminotransferase utilizes a different amino donor than the *E.coli* or *S. marcescens* enzyme. Under the assay conditions used, the specific activity of the *B. subtilis* DAPA aminotransferase was found to be 100-fold lower than that of the *E. coli* or *S. marcescens* enzyme. This low specific activity could be due to limiting concentrations of the amino donor in the extract.

Identification of Lysine as an Amino Donor for *B. subtilis* DAPA Aminotransferase To determine whether *B. subtilis* DAPA aminotransferase activity could be stimulated by addition of other amino donors to the reaction mix, various amino donors were screened for their ability to stimulate enzyme activity in vitro. A cell free extract prepared from a *B. subtilis* strain deleted for the bio operon but containing multiple copies (4–6) of the *B. subtilis* bioA gene transcribed from a phage SP01–26 promoter with the cassette integrated at the bpr locus, BI611 ($\Delta$bio:cat, bpr:[$P_{26}$bioA]$_{4-6}$), was dialyzed to remove any endogenous levels of the amino donor and the extract was assayed in the presence of each of the standard amino acids and several other amine compounds. Of twenty-six compounds tested, only L-lysine hydrochloride (>98% pure) stimulated DAPA aminotransferase activity (Table 1). In a subsequent experiment, various lysine derivatives and analogs were tested for stimulation of activity (Table 2). The ability of a more purified preparation of L-lysine(>99% pure) to stimulate activity supported the conclusion that L-lysine is an authentic amino donor for the enzyme and argued against the possibility that the true amino donor was a contaminant in the lysine preparation. The ability of the L-lysine analog, (S)-2-aminoethyl-L-cysteine (AEC), to stimulate activity further supported the conclusion that L-lysine is the true amino donor for *B subtilis* DAPA aminotransferase. The structure of (S)-2-aminoethyl-L-cysteine is identical to L-lysine except that the γ carbon has been replaced by a sulfur atom.

The use of lysine as an amino donor by *B. subtilis* DAPA aminotransferase distinguishes the enzyme from other bacterial DAPA aminotransferases (from *E.coli, S. marcescens*, and *B. sphaericus*), which use SAM as an amino donor.

Kinetic Studies of *B. subtilis* DAPA Aminotransferase.

The kinetic properties of *B. subtilis* DAPA aminotransferase were investigated using a crude cell-free extract prepared from BI611 ($\Delta$bio:cat, bpr:[$P_{26}$bioA]$_{4-6}$). The production of DAPA from KAPA and lysine was shown to be approximately linear with time. The conversion of substrate to product was approximately 10 to 40% in 20 minutes. The total amount of DAPA produced during a standard 20 minute reaction was shown to be directly proportional to the amount of protein added to the reaction mix. The pH optimum for the transamination reaction was determined to be pH 8.6. A linear relationship was demonstrated between KAPA concentration (<20 $\mu$M) and specific activity, when the lysine concentration was kept constant at saturating levels (19 mM) (FIG. 1). Enzyme activity leveled off at KAPA concentrations between 20 $\mu$m and 80 $\mu$M, and inhibition of activity was observed at KAPA concentrations above 80 $\mu$M. Substrate inhibition by KAPA has also been demonstrated for *E. coli* DAPA aminotransferase by Eisenberg and Stoner (1971, *J. Bacteriol.* 108:1135–1140). The *E. coli* enzyme was subject to inhibition by KAPA at levels above 20 $\mu$M. An approximately linear relationship was demonstrated between *B. subtilis* bioA enzyme activity and lysine concentration (0–20 mM) when the KAPA concentration was held constant. The enzyme became saturated for lysine at concentrations between 20 and 40 mM.

Figure 2:
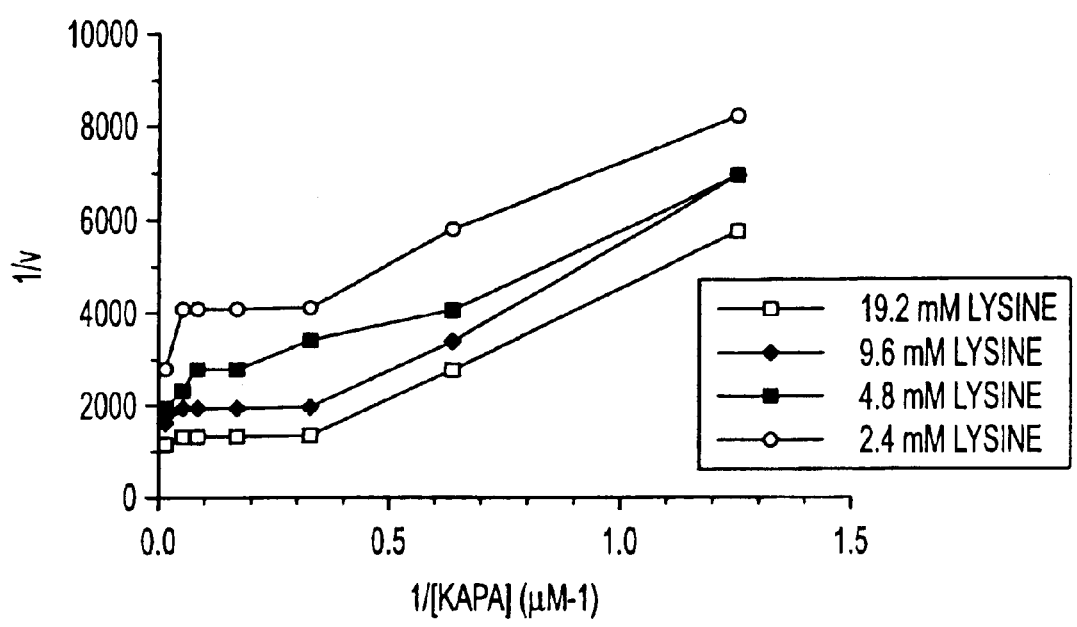
FIG. 2 is a reciprocal plot of initial velocity data for *B. subtilis* DAPA aminotransferase in the presence of varying concentrations of KAPA.

The substrate inhibition of *B. subtilis* DAPA aminotransferase by KAPA provides evidence for a double displacement or ping-pong reaction mechanism, as has been shown for *E.coli* DAPA aminotransferase (Stoner et al., J. Biol. Chem. 250:4037–4043, 1975). Additional evidence supporting this conclusion is provided by the experiment presented in FIG. 2. KAPA concentration was varied at four different fixed lysine concentrations, and initial velocity data was collected and plotted in a double reciprocal form. The lines are approximately parallel in the region of low KAPA concentration which is indicative of a ping-pong type reaction mechanism (Stoner et al., J. Biol. Chem. 250:4037–4043).

The apparent $K_m$ values for lysine and KAPA for the *B. subtilis* DAPA aminotransferase reaction were determined to be in the range of 2–25 mM and 1–5 μM, respectively. The $K_m$ of *E.coli* DAPA aminotransferase for KAPA was previously estimated to be 1.2 μM by Stoner and Eisenberg (1975, *J. Biol. Chem.* 250:4037–4043). The $K_m$ for lysine was difficult to measure accurately because KAPA is a substrate inhibitor which presumably competes with lysine for binding to the active site at low lysine concentrations. Nevertheless, the apparent $K_m$ of *B. subtilis* DAPA aminotransferase for lysine (2–25 mM) was significantly higher than the $K_m$ of the purified *E. coli* enzyme for SAM (0.2 mM), as determined by Stoner and Eisenberg (1975, *J. Biol. Chem.* 250:4037–4043). While not wishing to be bound by a particular mechanism, it appears that the *B. subtilis* DAPA aminotransferase has a relatively high $K_m$ for lysine, and that, in production strains which accumulate large amounts of KAPA, the *B. subtilis* DAPA aminotransferase is limited for lysine.

Fermentations of Strains with Enhanced *B. subtilis, E. coli,* or *S.marcescens* DAPA Aminotransferase Activity.

To test whether fermentations of the engineered biotin production strains were limited for the appropriate amino donors, a series of experiments were done in which lysine, methionine (the precursor to SAM), or lysine plus methionine were fed to fermentations of strains containing the appropriate bioA cassette and the level of KAPA-to-DAPA conversion was measured by vitamer bioassays and bioautography. These experiments were based in part on the hypothesis that the amino donor for the DAPA aminotransferase became limiting during fermentation resulting in a build-up of KAPA.

All fermentations were carried out in computer controlled 14 liter Chemap fermentors utilizing a dissolved oxygen control, glucose-limited fed-batch fermentation strategy. The fermentations were performed using medium described in Appendix 1. Pimelic acid, lysine, and methionine were also batched and fed in the fermentations as indicated. The HABA-avidin displacement assay was used to determine the total amount of dethiobiotin and biotin in shake flask and fermentation samples. Coupling this chemical assay with bioassays (as described in EP 635572, and Tanaka et al., *J. Micro. Methods* 6:237–247, 1987) that determine biotin levels allows an additional determination of dethiobiotin production.

The HABA-avidin displacement assay is based on two facts: 1) HABA absorbs more strongly at 500 nm when bound to avidin than when free in solution and 2) DTB or biotin will quantitatively displace HABA from avidin. The description of this assay is presented as Appendix 2. The HABA assay is linear from 2 to 14 mg/l of dethiobiotin (DTB).

Total vitamers were measured as DTB equivalents in fermentation samples that had been acidified before autolaving to prevent KAPA breakdown. Total vitamers were determined as described in EP 0635572A2.

Lysine-fed Fermentation of Strains with Enhanced *B. subtilis* BioA Activity.

The effect of lysine feed on KAPA-to-DAPA production was studied by using strains, BI282 and BI603, that overexpress *B. subtilis* DAPA aminotransferase. BI282 overexpresses all biotin biosynthetic genes on a multicopy cassette ($P_{15}$bio), integrated at the bio locus. BI603 is a derivative of BI282 containing multiple copies of an additional bioA cassette ($P_{26}$bioA) integrated at the bpr locus which further increases the levels of DAPA aminotransferase. Table 3 (top) shows the optical densities, biotin and vitamer production of BI603 and BI282 grown with 1 g/l pimelic acid and 6 g/liter lysine in both the batch and feed. The total vitamers produced by BI603 and BI282 with lysine in the batch and feed were about 1300 mg/l and 1000 mg/l, respectively. The biotin production of the three fermentations were comparable (20–22 mg/l). The levels of HABA vitamers (biotin+DTB) in lysine-batched fermentations were sharply higher compared to previous fermentations without lysine. Typically BI282 and BI603 produced between 20–40 mg/liter HABA vitamers. Addition of lysine increased HABA vitamer production of BI603 to 570 mg/l and BI282 to 330 mg/l. Based on the biotin titers, most of the HABA vitamers produced from lysine feeding appeared to be in the form of dethiobiotin. Since biotin is formed from dethiobiotin, the HABA titer represents the total production level of dethiobiotin in the cells (for simplicity dethiobiotin production and HABA vitamer titers will henceforth be used interchangeably). Bioautographies of 30 hour fermentation samples of BI603 confirmed the accumulation of dethiobiotin and showed that DAPA was not accumulated in large quantities (approximately 10 mg/l).

Methionine-fed Fermentation of Strains with Enhanced *E. coli* or *S. marcescens* BioA Activity.

The effect of methionine feed, the precursor to SAM, on the conversation of KAPA-to-DAPA was studied by fermentation of strains BI90 and BI96, expressing the *B. coli* or *S. marcescens* ATCC 31809 DAPA aminotransferase enzymes, respectively. BI90 (bio:$[P_{15}bio]_{7-8}$ sacB:$[P_{veg}bioA_{ec}]_1$) and BI96 (bio:$[P_{15}bio_{7-8}$ sacB: $[P_{veg}bioA_{sm}]_1$) are derivatives of BI282 that contain a single-copy *E. coli* $P_{veg}bioA_{ec}$ or *S. marcescens* $P_{veg}bioA_{sm}$ cassette, respectively, integrated at the sacB locus. 1 g/l pimelic acid and 3 g/l methionine were added to both the batch and feed; exogenous lysine was not added to these fermentations in order observe the effect on KAPA-to-DAPA conversion by only the gram-negative DAPA aminotransferases. As a negative control, BI282, which does not contain an engineered gram-negative bioA gene, was also grown under identical conditions. As shown in Table 4, total vitamer production of BI90, BI96, and BI282 was similar. Biotin production was slightly lower than usual (5–10 mg/l). The levels of HABA vitamers (biotin+DTB) in the methionine-fed fermentations of BI90 and BI96 were higher than the control BI282 fermentation. BI96 expressing the *S marcescens* ATCC 31809 $P_{veg}bioA_{sm}$ cassette produced 3–4-fold more HABA vitamers than BI282. BI90 expressing the *E coli* $P_{veg}bioA_{ec}$ cassette produced 5–6 fold higher levels of HABA vitamers. As with the previous lysine-fed fermentation of strains expressing the engineered *B. subtilis* bioA gene, most of the HABA vitamers were dethiobiotin. Addition of methionine to fermentation of strains with enhanced *E coli* or *S. marcescens* DAPA aminotransferase activity reduced the KAPA-to DAPA block presumably by increasing the level of SAM in the cell. Moreover, to the extent that the *B. subtilis* BioA enzyme synthesized from the engineered $P_{15}$bio operon in these strains is limited by insufficient lysine, conversion of KAPA-to-DAPA may increase when both lysine and methionine are fed to fermentations of BI90 or BI96.

Lysine and Methionine-fed Fermentations of Strains with Enhanced *B. subtilis* and *E. coli* BioA Activities.

The effect of combining both lysine and methionine, the precursor for SAM, on the conversion of KAPA-to-DAPA in fermentations of a strain, BI90, expressing both the *E. coli* and *B. subtilis* DAPA aminotransferases, was studied by adding 1 g/l pimelic acid, 6 g/l lysine, and 3 g/l methionine to both the batch and feed. As control fermentations, BI603 was grown with or without 6 g/l lysine in the batch and feed.

As shown in Table 5A, BI603 without added lysine produce little HABA vitamers (30 mg/l) of which about 10 mg/l was dethiobiotin. However, with the addition of lysine, dethiobiotin production in BI603 increased more than 10-fold (510 mg/l). Moreover, fermentation of BI90 with both lysine and methionine resulted in almost two-fold more dethiobiotin (930 mg/l) than fermentation of BI603 with lysine alone. The range of dethiobiotin production in BI90 fermentations with lysine and methionine and 1 g/l pimelic acid was about 600–900 mg/l, but in all cases the majority of the KAPA was converted to DTB.

Figure 3:
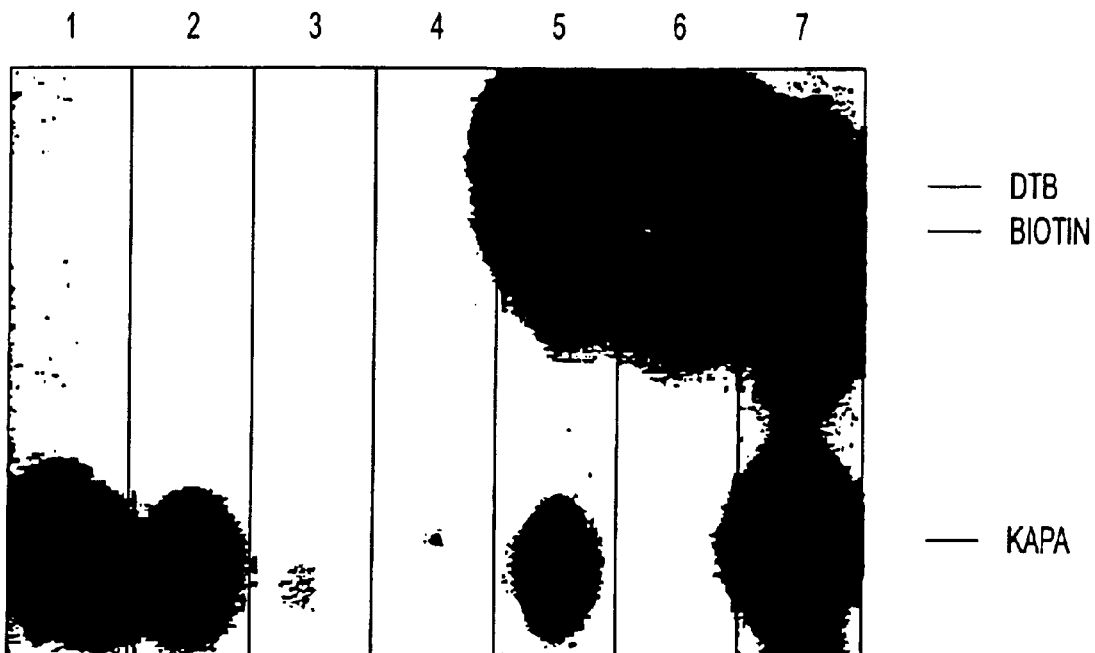
FIG. 3 is a representation of results from a bioautography of fermentation broths of different bacterial strains with lysine and methionine or with or without lysine, as described in Table 5.

The level of KAPA remaining in these strains was confirmed by analyzing the 30 hour fermentation samples by bioautography using *E. coli* ΔbioH as the indicator (FIG. 3 and Table 5B). In a separate bioautography using *E. coli* MEC1 indicator, DAPA was not detected in large quantities (15 mg/l for BI90 with lysine and methionine and 40 mg/l for BI603 with lysine; Table 6, bottom), consistent with earlier lysine-fed fermentations of BI603 (Table 3, bottom).

Lysine-fed Fermentations of Strains with Enhanced *B. subtilis* DAPA Aminotransferase Activity Grown in Amberex Based Medium.

We examined the effect of different amounts of added lysine on biotin, DTB (HABA vitamers) and vitamer production in BI282 grown in fermentation medium with Amberex instead of VY (Table 6). Under these fermentation conditions, the addition of lysine at 7.5 g/l in batch and feed was sufficient to yield approximately 100% conversion of KAPA to DTB. Addition of higher levels of lysine in the feed (24.8 g/l) did not appear to be required. Fermentations with added lysine and pimelic acid produced about 10-fold more DTB (660–780 mg/l) than a fermentation of BI282 without lysine (60 mg/l). The fermentation without lysine produced 2–3 fold more biotin (12 mg/l) than fermentations with 10-fold higher levels of DTB (4–5 mg/l biotin).

Construction of B1282 Derivatives That Overproduce Lysine.

We have also tried to increase the cell's lysine pool by an alterative method, namely boosting the internal lysine biosynthesis capacity. Strains of Brevibacter and Corynebacter have been developed to product about 80 g/l lysine, so it should be possible to engineer *B. subtilis* to overproduce lysine to the extent necessary to stimulate DTB synthesis. There are two basic approaches to take, 1) collect known mutants that are deregulated for lysine biosynthesis and move the relevant mutations into a biotin producing strain, and 2) isolate mutants deregulated for lysine production by selecting for lysine analog resistance directly in a biotin producing strain background.

Known Lysine Deregulated Mutants of *B. subtilis*.

The biosynthetic pathway from aspartate to lysine for *B. subtilis* is outlined in FIG. 4. The two regulated steps are the first step, catalyzed by aspartokinase, and the last step, which incidentally is the first step committed solely to lysine, catalyzed by diaminopimelate (DAP) decarboxylase. Both steps are regulated by feedback inhibition and at the level of gene expression. A summary of the regulated enzymes is given in Table 7.

Four types of mutations leading to deregulated lysine synthesis are known, 1) a DAP resistant aspartokinase I, 2) a constitutive aspartokinase II, 3) a lysine resistant DAP decarboxylase, and 4) an undefined S-2-aminoethyl-L-cysteine (AEC) resistant mutation that is unlinked to any of the known lysine genes. These known mutations are summarized in Table 7. The last three all have an AEC resistant phenotype, and so each could be moved into a biotin production strain by transduction, transformation, or congression.

Isolation of Lysine Overproducers Directly in Biotin Producing Strain Background.

Three out of the four classical cases of lysine deregulated mutants were isolated by selecting for lysine analog resistance. *B. subtilis* strains, PY79 (Youngman et al., Plasmid 12:1–9, 1984), BI282, and BI603 were tested for sensitivity to four lysine analogs, on minimal medium with no additive, with threonine, or with DAP plus threonine. The purpose of the additives was to focus the selection on the lysC gene, that encodes the lysine sensitive aspartokinase II. The only analog that inhibited growth under any conditions was AEC. All three strains behaved similarly; all were sensitive to AEC in all three media.

Spontaneous AEC resistant mutants were isolated from PY79, BI282, and BI603. The mutations in these strains are most likely to be lysC constitutive mutants, because according to the literature, most AEC resistance mutants are of that type. Eleven mutants from each parent were tested for lysine secretion in a minimal medium. The assay used was a biological assay using *B. subtilis* 1A615 (trpC2 lys:Tn917) as an indicator strain. None of the parent strains secreted lysine detectable by the assay (<2 mg/l). However, 10 out of 11 PY79 mutants secreted lysine in the range of 20 to 70 mg/l, one BI282 mutant secreted 30 mg/l and one BI603 mutant secreted 26 mg/l lysine. The BI282 and BI603 mutants, called BI641 and BI642, were then tested for biotin production in the fermentor without a lysine feed and compared to BI282 with a lysine feed. As shown in Tables 5, 6, and 8, BI641 and BI642 produced a higher level of DTB than the respective parent strains in the absence of lysine, but not as much as when 6 g/l lysine was fed. Lysine biosynthesis can be further deregulated by introducing a second lysine deregulating mutation as described above.

Deposit Statement

The subject cultures listed below are deposited under conditions that assure that access to the cultures will be available during the pendency of the patent application disclosing them to one determined by the Commissioner of Patents and Trademarks to be entitled thereto under 37 C.F.R. 1.14 and 35 U.S.C. 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposits, and in any case, for a period of at least 30 (thirty) years after the date of deposit or or the enforceable life of any patent which may issue disclosing the cultures plus five years after the last request for a sample from the deposit. The depositor acknowledges the duty to replace the deposits should the depository be unable to furnish a sample when requested, due to the condition of the deposits. All restrictions on the availability to the public of the subject culture deposits will be irrecovably removed upon the granting of a patent disclosing them.

The subject cultures listed below have been deposited at the American Type Culture Collection (ATCC), which at the time of deposit was located at 12301 Parklawn Dr., Rockville, Md. 20852, U.S.A., and which is now located at 10801 University Blvd., Manassas, Va. 20110-2209, U.S.A.

| Strain | ATCC No. |
|--------|----------|
| BI 90  | 55999    |
| BI 96  | 202000   |
| BI 603 | 202003   |
| BI 641 | 202002   |
| BI 642 | 202001   |
| BI 282 | 55574    |

Other embodiments are within the following claims.

APPENDIX I

Medium composition for biotin and vitamers production in bench scale fermentors.

| Medium Component | Concentration Batch | Feed |
|------------------|-------|------|
| Glucose | 15.0 g/liter | 750 g/liter |
| Veal Infusion Broth[1] | 25.0 g/liter | — |
| Yeast Extract[1] | 5.0 g/liter | — |
| Sodium Glutamate | 5.0 g/liter | — |
| $KH_2PO_4$ | 7.5 g/liter | 13.7 g/liter |
| $M_gCl.6H_2O$ | 1.0 g/liter | 1.5 g/liter |
| $(NH_4)_2SO_4$ | 2.0 g/liter | — |
| MAZU DF-37C | 2.5 g/liter | — |
| $CaCl_2.2H_2O$ | 1.0 g/liter | — |
| $CuSO_4.5H_2O$ | 0.4 mg/liter | 4.0 mg/liter |
| $ZnSO_4.7H_2O$ | 0.5 mg/litr | 5.0 mg/liter |
| $MnSO_4.H_2O$ | 25.0 mg/liter | 35.0 mg/liter |
| $CoCl_2.6H_2O$ | 1.0 mg/liter | 10.0 mg/liter |
| Sodium Molybdate-$2H_2O$ | 0.2 mg/liter | 2.0 mg/liter |
| $FeSO_4.7H_2O$ | 50.0 mg/liter | 100.0 mg/liter |
| Sodium Citrate-$2H_2O$ | 50.0 mg/liter | 100.0 mg/liter |

[1]In amberex Medium the Veal Infusion Broth and Yeast Extract are replaced with 10 g/l Amberex 695.

APPENDIX II

Protocol of avidin-HABA [2-(4-hydroxyphenylazo) benzoic acid] displacement assay for biotin and dethiobiotin.

Reagents and Solutions:

Buffer: 0.1M $NaPO_4$, pH 7.0.
Avidin: From Sigma (Cat # A-9275). Dissolved at 5 mg/ml in Buffer.
HABA: From Aldrich (Cat # 14,803-2). Dissolved at 0.375M in water + 1 eq. NaOH.

| Prepare Mix: | 20 samples | 50 samples |
|--------------|------------|------------|
| Avidin | 1 ml | 2.5 ml |
| HABA | 0.08 ml | 0.2 ml |
| Buffer | 38.9 ml | 97.3 ml |

Assay:

Zero spectrophotometer;
Add 2 ml of Buffer to disposable 5 ml cuvette; record $OD_{500}$.

APPENDIX II-continued

Protocol of avidin-HABA [2-(4-hydroxyphenylazo) benzoic acid] displacement assay for biotin and dethiobiotin.

To read sample:

Place disposable 5 ml cuvette in spectrophotometer.
Add 2 ml of Mix; stir; record $OD_{500}$.
Add sample in 0.1 ml volume; stir; record $OD_{500}$.

Standards:

Use 0.1 ml DTB at 2 mg/ml to 14 mg/ml as samples.
Use 0.1 ml Buffer as "zero" point.

Calculations:

Calculate $\Delta OD_{500}$ minus $\Delta OD_{500}$.
Plot standards and use curve to determine HABA vitamers from samples.

Notes:

1. Useful range is 2 to 14 mg/l of biotin + dethiobiotin.
2. Add mix to cuvette, read OD500, and then add sample and mix without removing cuvette from the spectrophotometer.
3. Best results are obtained when a constant volume is used with a set of samples and standards. Use Buffer to bring all samples to the same volume.

TABLE 1

| Amino donor tested | Stimulation of activity | Amino donor tested | Stimulation of activity |
|--------------------|-------------------------|--------------------|-------------------------|
| none | – | L-glutamic acid | – |
| L-methionine | – | L-lysine | + |
| L-aspartic acid | – | L-tryptophan | – |
| L-asparagine | – | L-valine | – |
| L-tyrosine | – | L-leucine | – |
| L-cysteine | – | L-alanine | – |
| L-proline | – | L-isoleucine | – |
| L-serine | – | L-ornithine | – |
| L-glycine | – | L-homoserine | – |
| L-glutamine | – | DL-homocysteine | – |
| L-threonine | – | spermine | – |
| L-histidine | – | S-adenosyl-L-methionine | – |
| L-phenylalanine | – | S-adenosyl-L-homocysteine | – |
| L-arginine | – | | |

TABLE 2

| Compound added to extract | DAPA aminotransferase specfic activity (nmoles/min/mg) |
|---------------------------|--------------------------------------------------------|
| none | 0 |
| L-lysine (>98%) | 0.76 |
| L-lysine (>99%) | 0.56 |
| D-lysine (>98%) | 0.19 |
| DL-lysine (>98%) | 0.35 |
| Nα-acetyl-L-lysine | 0 |
| Nε-acetyl-L-lysine | 0 |
| Nε-methyl-L-lysine | 0 |
| gly-lys | 0 |
| lys-gly | 0 |
| (S)-2-aminoethyl-L-cysteine | 0.48 |
| diaminopimelic acid | 0 |

TABLE 3

| Fermentation #/ Strain | Lysine (6 g/liter) Batch | Lysine (6 g/liter) Feed | Time (hr) | OD$_{600}$ | Total Vitamers (mg/liter) | Biotin (mg/liter) | HABA Vitamers (mg/liter) | Calculated DTB (mg/liter) |
|---|---|---|---|---|---|---|---|---|
| B160/BI603 | + | − | 24 | 150 | 740 | 16 | 330 | 314 |
| B160/BI603 | + | − | 30 | 160 | 950 | 22 | 400 | 378 |
| B161/BI603 | + | + | 24 | 140 | 1100 | 14 | 420 | 406 |
| B161/BI603 | + | + | 30 | 160 | 1290 | 20 | 570 | 550 |
| B162/BI282 | + | + | 24 | 132 | 1100 | 10 | 220 | 210 |
| B162/BI282 | + | + | 30 | 140 | 1000 | 22 | 330 | 308 |

| | | | | Vitamer Breakdown | | | | |
|---|---|---|---|---|---|---|---|---|
| Fermentation #/ Strain | Lysine (6 g/liter) Batch | Lysine (6 g/liter) Feed | Time (hr) | KAPA (mg/liter) | DAPA[a] (mg/liter) | DTB (mg/liter) | Biotin (mg/liter) | Total (mg/liter) |
| B161/BI603 | + | + | 30 | 710 | 10 | 550 | 20 | 1290 |

[a]Estimated from bioautography of a an acid autoclaved sample using *E. coli* MEC1 indicator.

TABLE 4

| Fermentation #/ Strain | Time (hr.) | OD$_{600}$ | Total Vitamers (mg/liter) | Biotin (mg/liter) | HABA Vitamers (mg/liter) | Calculated DTB (mg/liter) |
|---|---|---|---|---|---|---|
| BI63/BI90 | 24 | 150 | 760 | 8 | 126 | 118 |
| BI63/BI90 | 30 | 160 | 720 | 9 | 145 | 136 |
| BI64/BI96 | 24 | 170 | 830 | 9 | 84 | 75 |
| BI64/BI96 | 30 | 160 | 850 | 10 | 88 | 78 |
| BI65/BI282 | 24 | 140 | 610 | 5 | 17 | 12 |
| BI65/BI282 | 30 | 150 | 590 | 6 | 25 | 19 |

TABLE 5A

| | Batch and Feed | | | | | | | |
|---|---|---|---|---|---|---|---|---|
| Fermentation #/ Strain | Lys (6 g/liter) | Met (3 g/liter) | Time (hr) | OD$_{600}$ | Total Vitamers (mg/liter) | Biotin (mg/liter) | HABA Vitamers (mg/liter) | Calculated DTB (mg/liter) |
| B166/BI603 | − | − | 24 | 150 | 800 | 20 | 30 | 10 |
| B166/BI603 | − | − | 30 | 155 | 600 | 21 | 30 | 9 |
| B167/BI603 | + | − | 24 | 143 | 800 | 6 | 460 | 454 |
| B167/BI603 | + | − | 30 | 166 | 870 | 5 | 510 | 506 |
| B168/BI90 | + | + | 24 | 128 | 800 | 5 | 890 | 885 |
| B168/BI90 | + | + | 30 | 165 | 1000 | 5 | 930 | 925 |

TABLE 5B

| | | | | Vitamer Breakdown | | | | |
|---|---|---|---|---|---|---|---|---|
| | Batch and Feed | | | KAPA (mg/liter) | | | | |
| Fermentation #/ Strain | Lys (6 g/liter) | Met (3 g/liter) | Time (hr) | a | b | DAPA[c] (mg/liter) | DTB (mg/liter) | Biotin (mg/liter) | Total (mg/liter) |
| B166/BI603 | − | − | 30 | 570 | 470 | 0 | 9 | 21 | 600 |
| B167/BI603 | + | − | 30 | 320 | 250 | 40 | 505 | 5 | 870 |
| B168/BI90 | + | + | 30 | 55 | 60 | 15 | 925 | 5 | 1000 |

[a]Calculated by subtracting DAPA, DTB, and biotin titers from total vitamers.
[b]Estimated from bioautography of acid autoclaved samples using *E. coli* ΔbioH indicator.
[c]Estimated from bioautography of acid autoclaved samples using *E. coli* MEC1 indicator.

TABLE 6

| Run/Strain | Lysine (g/liter) Batch | Lysine (g/liter) Feed | Time (hr.) | OD$_{600}$ | Total Vitamers (mg/liter) | HABA Vitamers (mg/liter) | Biotin (mg/liter) | % KAPA to DTB conversion (mg/liter) |
|---|---|---|---|---|---|---|---|---|
| B235/B1282 (CAM60) | 7.5 | 24.8 | 24 | 107 | 590 | 600 | 4 | 100 |
|  |  |  | 30 | 122 | 830 | 660 | 4 | 89 |
| B236/B1282 (CAM60) | — | — | 24 | 123 | 410 | 40 | 11 | 10 |
|  |  |  | 30 | 130 | 450 | 60 | 12 | 13 |
| B237/B1282 (CAM60) | 7.5 | 7.5 | 24 | 115 | 630 | 780 | 4 | 100 |
|  |  |  | 30 | 124 | 670 | 750 | 5 | 100 |

*Batch medium (Amberex) contained 1 g/l pimelic acid and the indicated lysine amount; Feed medium contained 1 g/l pimelic acid and the indicated lysine amount.

TABLE 7

| Enzyme | Type of Mutation | Gene | Map Location | Inhibitor | Corepressor | Decrease in stationary |
|---|---|---|---|---|---|---|
| Aspartokinase I | DAP$^r$ | dapG | 149 | DAP | none known | no |
| Aspartokinase II | constitutive | lysC | 252 | lysine | lysine | yes |
| Aspartokinse III | — | — | — | lysine & threonine | threonine | yes |
| DAP decarboxylase | lys$^r$ | lysA | 210 | lysine | lysine & ? | yes |
| — | — | aecB | 282 | — | — | — |

TABLE 8

| Fermentation #/ Strain | Lysine (6 g/liter) Batch | Lysine (6 g/liter) Feed | Time (hr) | OD600 | Total Vitamers (mg/liter) | Biotin (mg/liter) | HABA Vitamers (mg/liter) | Calculated DTB (mg/liter) |
|---|---|---|---|---|---|---|---|---|
| B190/BI282 | + | + | 24 | 84 | 240 | 6 | 270 | 264 |
| B190/BI282 | + | + | 30 | 125 | 390 | 7 | 360 | 353 |
| B191/BI641 (BI282aec7) | – | – | 24 | 74 | 470 | 5 | 130 | 125 |
| B191/BI641 (BI282aec7) | – | – | 30 | 129 | 500 | 6 | 144 | 138 |
| B192/BI642 (BI603aec11) | – | – | 24 | 86 | 540 | 4 | 160 | 156 |
| B192/BI642 (BI603aec11) | – | – | 30 | 120 | 560 | 5 | 110 | 105 |

What is claimed is:

1. A method of producing a biotin vitamer by:
   (a) culturing a bacterium comprising a *Bacillus subtilis* lysine-utilizing diaminopelargonic acid (DAPA) aminotransferase, said culturing taking place in an environment wherein lysine, a lysine analog, or a lysine precursor is exogenously added to the culture to provide a concentration of at least 10 mmoles lysine, lysine analog, or lysine precursor per liter of culture during the entire culturing step; and
   (b) recovering said biotin vitamer.

2. A method of producing a biotin vitamer by:
   (a) culturing a bacterium comprising a *Bacillus subtilis* lysine-utilizing DAPA aminotransferase, wherein the lysine biosynthetic pathway is deregulated in said bacterium; and
   (b) recovering said biotin vitamer.

3. The method of claim 1 in which the bacterium is engineered to overproduce a *Bacillus subtilis* lysine-utilizing DAPA aminotransferase.

4. The method of claim 2 in which the bacterium is engineered to overproduce a *Bacillus subtilis* lysine-utilizing DAPA aminotransferase.

5. The method of claim 2 or claim 4, wherein lysine, a lysine analog, or a lysine precursor is exogenously added to the culture.

6. The method of claim 2 or claim 4, in which lysine, a lysine analog, or a lysine precursor is exogenously added to the culture to provide a concentration of at least 10 mmoles lysine, lysine analog, or lysine precursor per liter of culture during the entire culturing step.

7. The method of claim 1, claim 2, claims 3, or claim 4, in which the biotin vitamer is biotin, dethiobiotin, or diaminopelargonic acid (DAPA).

8. The method of claim 1, claim 2, claim 3, or claim 4, in which the biotin vitamer is dethiobiotin, and, after recovering the dethiobiotin, the method further comprises converting the recovered dethiobiotin to biotin by a separate fermentation, biochemical reaction, or chemical reaction, and recovering biotin.

9. The method of claim 1, claim 2, claim 3, or claim 4, in which the bacterium is resistant to a lysine analog.

10. The method of claim 9, wherein said analog is S-2-aminoethyl-L-cysteine (AEC).

11. The method of claim 1 or claim 2, wherein at least one biotin synthetic pathway steps in addition to expression of a polynucleotide encoding a DAPA aminotransferase, is deregulated in said bacterium.

12. The method of claim 1, claim 2, claim 3, or claim 4, in which the biotin vitamer is biotin, and the method comprises recovering and purifying the biotin.

13. The method of claim 1, claim 2, claim 3, or claim 4, wherein said bacterium is further engineered to produce a s-adenosylmethionine (SAM)-utilizing DAPA aminotransferase.

14. The method of claim 13 in which methionine, S-adenosylmethionine (SAM), or an analog of SAM is added to the culture.

15. The method of claim 13 wherein lysine, a lysine analog, or a lysine precursor is added to the culture.

16. The method of claim 14, wherein lysine, a lysine analog, or a lysine precursor is added to the culture.

17. The method of claim 15 in which lysine or a lysine analog exogenously added to the culture provides a concentration of at least 10 mmoles lysine or lysine analog per liter of culture during the entire culturing step.

18. The method of claim 16 in which lysine or a lysine analog exogenously added to the culture provides a concentration of at least 10 mmoles lysine or lysine analog per liter of culture during the entire culturing step.

19. The method of claim 13 in which the biotin vitamer is biotin, dethiobiotin, or diaminopelargonic acid (DAPA).

20. The method of claim 13 in which the biotin vitamer is dethiobiotin, and, after recovering the dethiobiotin, the method further comprises converting the recovered dethiobiotin to biotin by a separate fermentation, biochemical reaction, or chemical reaction, and recovering biotin.

21. The method of claim 13 wherein at least one biotin synthetic pathway step, other than expression of a polynucleotide encoding a DAPA aminotransferase, is deregulated in said bacterium.

22. The method of claim 13 in which the biotin vitamer is biotin, and the method comprises recovering and purifying the biotin.

* * * * *